US00PP19282P2

(12) United States Plant Patent
Kobayashi

(10) Patent No.: US PP19,282 P2
(45) Date of Patent: Oct. 7, 2008

(54) POINSETTIA PLANT NAMED 'PER1124'

(50) Latin Name: *Euphorbia pulcherrima*
Varietal Denomination: PER1124

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/804,337

(22) Filed: May 17, 2007

(51) Int. Cl.
*A01H 5/00* (2006.01)

(52) U.S. Cl. ..... Plt./306; Plt./303

(58) Field of Classification Search ..... Plt./306, Plt./303
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of Poinsettia plant named 'PER1124', characterized by its compact, upright and mounded plant habit; recurved dark green-colored leaves; inflorescences with recurved pink-colored flower bracts with darker pink-colored speckles; early to mid-season flowering; natural season flower maturity date is late November for plants grown in Encinitas, Calif.; and excellent post-production longevity.

1 Drawing Sheet

Botanical designation: *Euphorbia pulcherrima.*
Cultivar denomination: 'PER1124'.

BACKGROUND OF THE INVENTION

The present invention relates to a new and distinct cultivar of Poinsettia plant, botanically known as *Euphorbia pulcherrima* Willd., and hereinafter referred to by the name 'PER1124'.

The new Poinsettia a product of a planned breeding program conducted by the Inventor in Encinitas, Calif. The objective of the breeding program is to create new Poinsettia cultivars having strong stems, recurved leaves and flower bracts, attractive flower bract coloration, uniform plant habit and excellent post-production longevity.

The new Poinsettia originated from a cross-pollination made by the Inventor in December, 2001 of a proprietary selection of *Euphorbia pulcherrima* Willd. identified as code number V-75, not patented, as the female, or seed, parent, with the Poinsettia cultivar PER1072, disclosed in U.S. Plant Pat. No. 15,883, as the male, or pollen, parent. The cultivar PER1124 was discovered and selected by the Inventor as a flowering plant within the progeny of the stated cross-pollination in a controlled environment in Encinitas, Calif. in December, 2002. The selection of this plant was based on its attractive flower bract colors and good plant form and substance.

Asexual reproduction of the new Poinsettia by terminal vegetative cuttings in a controlled environment in Encinitas, Calif. since January, 2003, has shown that the unique features of this new Poinsettia are stable and reproduced true to type in successive generations of asexual reproduction.

SUMMARY OF THE INVENTION

The cultivar PER1124 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER1124'. These characteristics in combination distinguish 'PER1124' as a new and distinct cultivar of Poinsettia:

1. Compact, upright and mounded plant habit.
2. Recurved dark green-colored leaves.
3. Inflorescences with recurved pink-colored flower bracts with darker pink-colored speckles.
4. Early to mid-season flowering; natural season flower maturity date is late November for plants grown in Encinitas, Calif.
5. Excellent post-production longevity.

Plants of the new Poinsettia differ from plants of the female parent selection primarily in leaf and flower bract color as plants of the female parent selection have lighter green-colored leaves and mauve pink-colored flower bracts.

Plants of the new Poinsettia differ primarily from plants of the male parent, the cultivar PER1072, primarily in flower bract color as plants of the cultivar PER1072 have dark red-colored flower bracts.

Plants of the new Poinsettia can be compared to plants of the cultivar Windark, disclosed in U.S. Plant Pat. No. 12,546. In side-by-side comparisons conducted in Encinitas, Calif. plants of the new Poinsettia differed in flower bract color and time to flower as plants of the new Poinsettia had dark red-colored flower bracts and flowered about two weeks earlier than plants of the cultivar Windark.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the bottom of the sheet comprises a side perspective view of a typical flowering plant of 'PER1124' grown in a container.

The photograph at the top of the sheet is a close-up view of a typical inflorescence of 'PER1124'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The aforementioned photographs, following observations and averaged measurements describe plants grown in Encinitas, Calif. during the winter under commercial practice in a polyethylene-covered greenhouse with day temperatures averaging about 24° C., night temperatures averaging about 19° C. and light levels about 4,000 foot-candles. Single plants were grown in 16.5-cm pots and pinched once. Plants were flowered under natural season short day/long night conditions. Plants were about 21 weeks from unrooted cuttings when the photographs and the detailed botanical description were taken. In the following description, color references are made to The Royal Horticultural Society Colour Chart, 1995 Edition, except where general terms of ordinary dictionary significance are used.

Botanical classification: *Euphorbia pulcherrima* Willd. cultivar PER1124.

Parentage:

*Female parent.*—Proprietary selection of *Euphorbia pulcherrima* Willd. identified as code number V-75, not patented.

*Male parent.*—*Euphorbia pulcherrima* Willd. cultivar PER1072, disclosed in U.S. Plant Pat. No. 15,883.

Propagation:

*Type cutting.*—Vegetative terminal cuttings.

*Time to initiate roots.*—About 10 days at 20° to 22° C.

*Time to develop roots.*—About 28 days at 20° C. to 22° C.

*Root description.*—Thick, fibrous, freely-branching; white in color.

Plant description:

*Plant form/growth habit.*—Compact, upright; top of plant mounded; inverted triangle. Vigorous growth habit.

*Plant height.*—About 39 cm.

*Plant diameter or spread.*—About 35 cm.

*Lateral branch description.*—Quantity: About six lateral branches develop after pinching. Length: About 29 cm. Diameter: About 6 mm. Internode length: About 2 cm. Strength: Strong. Texture: Smooth; glabrous. Color: 146A.

*Foliage description.*—Arrangement: Alternate, single. Length: About 9.5 cm. Width: About 8 cm. Shape: Elliptic. Apex: Acuminate. Base: Obtuse with cordate tendencies. Margin: Entire. Venation pattern: Pinnate. Texture, upper and lower surfaces: Glabrous, smooth. Surface: Rugose. Aspect: Recurved. Color: Developing foliage, upper surface: 146A. Developing foliage, lower surface: 146B. Fully expanded foliage, upper surface: Darker than 147A; venation, 147B. Fully expanded foliage, lower surface: 147A; venation, 147C. Petiole: Length: About 3 cm. Diameter: About 3.5 mm. Texture, upper and lower surfaces: Smooth; glabrous. Color, upper and lower surfaces: 146B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early to mid-season flowering habit; response time is about eight weeks; natural season flower maturity date is late November for plants grown in Encinitas, Calif.

*Post-production longevity.*—Plants of the new Poinsettia maintain good substance and bract color for about four weeks under interior conditions.

*Inflorescence size.*—Diameter: About 14 cm. Height (depth): About 9 cm.

*Flower bracts.*—Quantity per inflorescence: About 28. Length, largest bracts: About 6 cm. Width, largest bracts: About 6 cm. Shape: Elliptic. Apex: Acuminate. Base: Obtuse. Margin: Entire. Texture, upper and lower surfaces: Glabrous, smooth. Surface: Rugose. Aspect: Recurved. Venation pattern: Pinnate. Color: Developing or transitional bracts, upper surface: 50A. Developing or transitional bracts, lower surface: 50C. Fully developed bracts, upper surface: 50C; random speckles, 50A and 50B. Fully developed bracts, lower surface: 50C; random speckles, 50B. Venation, upper and lower surfaces: Similar to flower bract color. Bract petiole: Length: About 1.8 cm. Diameter: About 2.5 mm. Texture, upper and lower surfaces: Smooth; glabrous. Color: 145B.

*Cyathia.*—Quantity per corymb: About twelve. Diameter of cyathia cluster: About 2 cm by 3 cm. Length: About 1 cm. Width: About 6 mm. Shape: Ovoid. Color, immature: 146D. Color, mature: 145A. Nectaries: Quantity per cyathium: About one or two. Size: About 3 mm by 5 mm. Color: 14A.

*Peduncle.*—Length: About 5 mm. Diameter: About 2 mm. Strength: Strong. Aspect: Mostly upright. Texture: Smooth; glabrous. Color: 146D.

*Reproductive organs.*—Stamens: Quantity per cyathium: About 15. Anther shape: Bi-lobed. Anther length: About 1 mm. Anther color: 163C. Amount of pollen: Scarce. Pollen color: 13A. Pistils: None observed. Seed: Seed development has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 30° C.

It is claimed:

1. A new and distinct Poinsettia plant named 'PER1124' as illustrated and described.

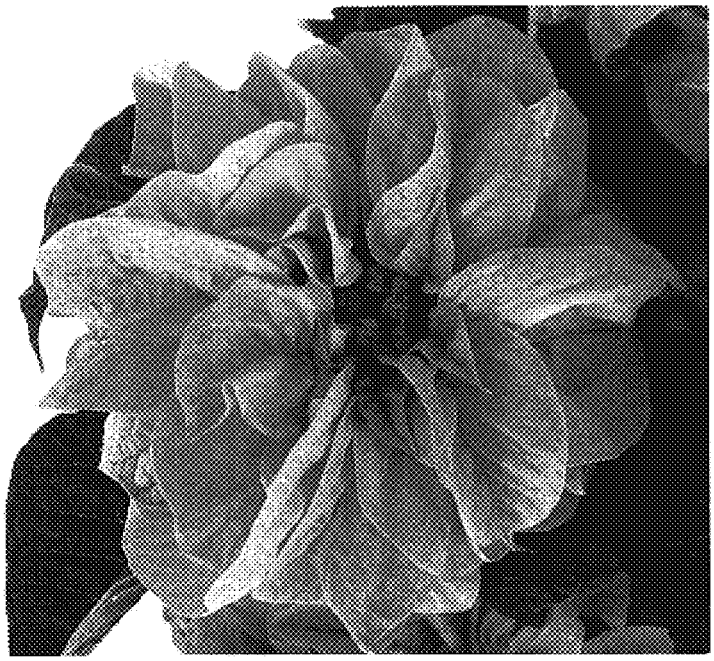
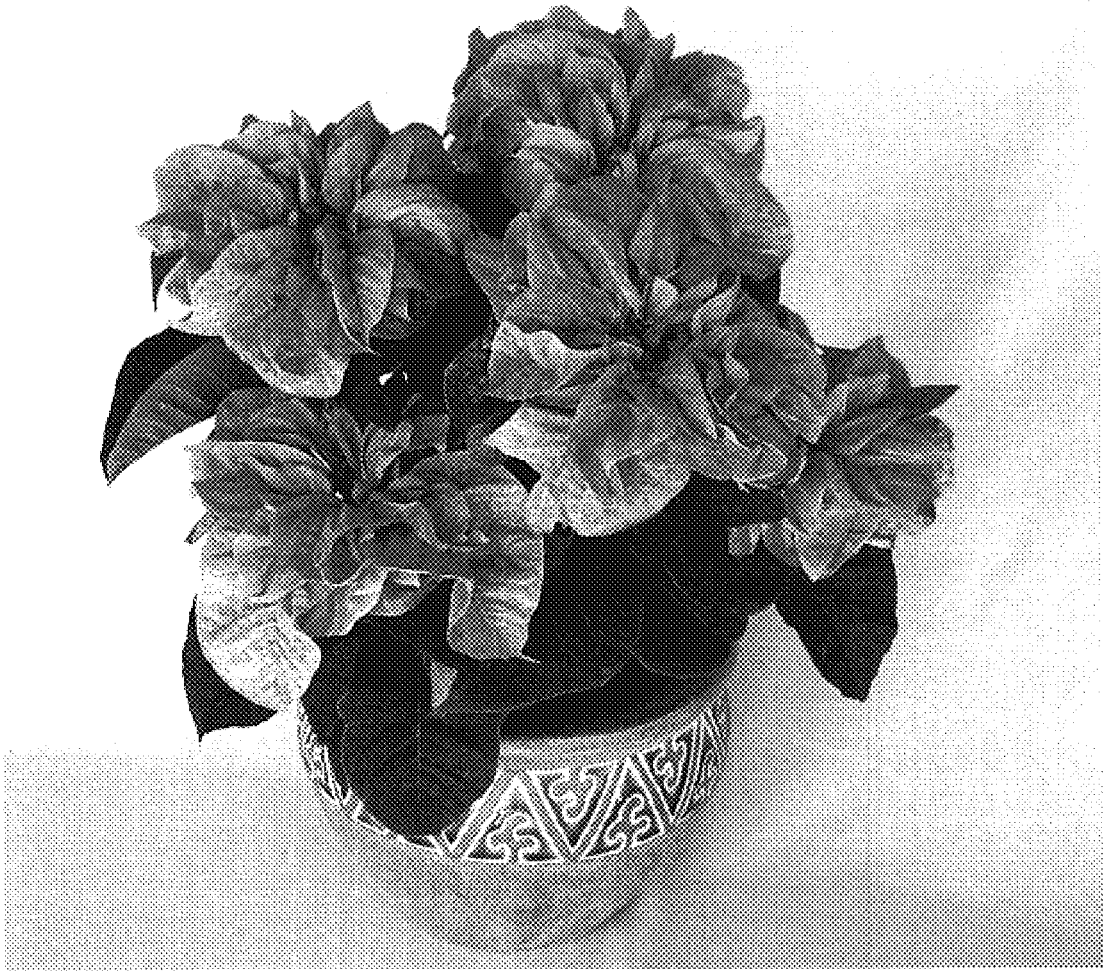

* * * * *